United States Patent [19]

Hiraoka et al.

[11] Patent Number: 4,769,776

[45] Date of Patent: Sep. 6, 1988

[54] APPARATUS FOR MEASURING THE CONCENTRATION OF FILAMENTOUS MICROORGANISMS IN A MIXTURE INCLUDING MICROORGANISMS

[75] Inventors: Masakatsu Hiraoka, Uji; Kazushi Tsumura, Nagaokakyo; Kenji Baba; Shoji Watanabe, both of Hitachi; Mikio Yoda; Ibaraki; Naoki Hara, Hitachi, all of Japan

[73] Assignee: Hitachi, Ltd., Tokyo, Japan

[21] Appl. No.: 900,420

[22] Filed: Aug. 26, 1986

[30] Foreign Application Priority Data

| Aug. 30, 1985 | [JP] | Japan | 60-189603 |
| Aug. 30, 1985 | [JP] | Japan | 60-189604 |
| Aug. 30, 1985 | [JP] | Japan | 60-189605 |
| Aug. 30, 1985 | [JP] | Japan | 60-189606 |
| Aug. 30, 1985 | [JP] | Japan | 60-189608 |

[51] Int. Cl.$^4$ .................................... G01N 15/00
[52] U.S. Cl. ............................ 364/555; 210/85; 364/413.01
[58] Field of Search ............. 210/96.1, 85; 382/16, 382/18, 22, 53, 60; 364/413, 555

[56] References Cited

U.S. PATENT DOCUMENTS

| 3,609,685 | 9/1971 | Deutsch | 382/60 X |
| 3,968,475 | 7/1976 | McMahon | 382/18 X |
| 4,564,444 | 1/1986 | Hiraoka | 210/96.1 |
| 4,574,393 | 3/1986 | Blackwell | 382/18 X |
| 4,654,139 | 3/1987 | Baba | 210/96.1 X |

Primary Examiner—Jerry Smith
Assistant Examiner—Steven Kibby
Attorney, Agent, or Firm—Antonelli, Terry & Wands

[57] ABSTRACT

The image of microorganisms contained in a sludge of an aeration tank is picked up by an image pickup device having the function of magnifying and picking up microorganism images. Binarizing processing is then made to obtain a binarized image from the resulting gray image, and the binarized image is subjected to thinning processing. The number of pixels of the image left after often the thinning processing is counted to measure the amount of filamentous microorganisms. In this manner, the amount of the filamentous microorganisms can be measured accurately irrespective of their thickness.

16 Claims, 16 Drawing Sheets (a) (b) (c) (d)

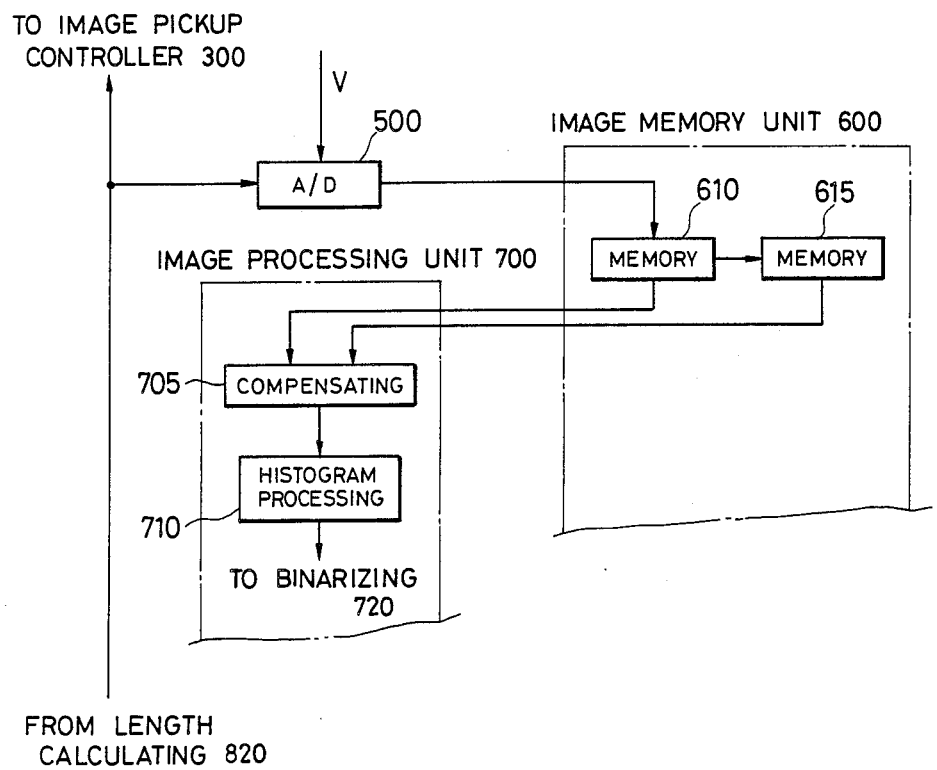

APPARATUS FOR MEASURING THE CONCENTRATION OF FILAMENTOUS MICROORGANISMS IN A MIXTURE INCLUDING MICROORGANISMS

BACKGROUND OF THE INVENTION

1. Field of the Invention

This invention relates generally to an apparatus for measuring the concentration of filamentous microorganisms in a mixture containing the microorganisms, and more particular ularly to an apparatus for measuring the concentration of the filamentous microorganisms by use of an image processing technique.

2. Description of the Prior Art

In a sewage treatment plant, aeration is made by blowing air into inflowing water inside an aeration tank, organic matters contained in the inflowing water are absorbed by miroorganisms and removed from the water and after the microorganisms are sedimented in a sedimentation basin, a supernatant is discharged. It is therefore necessary to keep those microorganisms which absorb the organic matters well and have high sedimentability. These microorganisms are broadly classified into zoogleal microorganisms and filamentous microorganisms. Among them, if the filamentous microoganisms increase too much (which is called "bulking"), sedimentability drops. If sedimentability drops, the microorganisms will outflow from the sedimentation basin. Accordingly, it is of importance to limit the increase of the filamentous microorganisms. An example of such microorganisms is Sphaerotilus. If the filamentous microorganisms increase too much in the sewage treating process, various problems such as deterioration of the treated water quality and the outflow of the microorganisms will occur.

In a cultivation process of microorganisms, on the other hand, cultivation of filamentous microorganisms is made so as to produce antibiotics such as penicillin, or fermentation is made by utilizing the filamentous microorganisms. These processes are directed to obtain the antibiotics metabolized from the filamentous microorganisms by cultivating them. However, since the amount of the antibiotics cannot be measured within a short period, it is necessary to supervise whether or not the filamentous microorganisms increase.

In both the sewage treating process and the microorganism cultivation process described above, measurement of the amount of the filamentous microorganisms is important for the operation management of these process. At present, the length or the amount of the filamentous microorganisms has been measured by a manual operation of a supervisor (a supervising person). In the sewage treating process, for example, it has been customary to measure the length of the filamentous microorganisms on a photograph by the use of a curvometer or by observation through a microscope. In the microorganism cultivation process, on the other hand, the filamentous microorganisms are sampled and dried, and the dry weight is measured.

Since the conventional measuring method relies on the manual operation by the supervisor, however, several hours of time is necessary for the measurement even by a skilled supervisor. Accordingly, continuous supervision and early detection cannot be made and the management of the cultivation state of the filamentous microorganisms cannot be made, either.

To solve the problems described above, the Applicants of the present invention proposed previously a method of measuring the length of the filamentous microorganisms in Japanese Patent Application No. 140423/1983 (Japanese Patent Laid-Open No. 31889/1985) corresponding to U.S. Pat. No. 4,564,444. This method detects the magnified image of the microorganisms by an industrial television (ITV) camera and recognizes the filamentous microorganisms by the application of an image processing technique.

More definitely, after the image of the filamentous microorganisms is enlarged, the filamentous microorganisms are identified by image processing to extract corresponding pixels, and the recognized pixels are accumulated and then converted to the amount of the filamentous microorganisms. Though the filamentous microorganisms appear filamentary, a certain thickness exists in the filamentary portion. Therefore, the amount of the filamentous microorganisms must be calculated from the number of accumulated pixels in order to accurately measure their amount.

Generally, magnification is adjusted in such a manner that the thickness of the filamentous microorganisms corresponds to one pixel, but the thickness corresponds in practice to one to three pixels due to illumination nonuniformity and noise. In other words, the thickness of the recognized filamentous microorganisms corresponds to one to three pixels. For this reason, even if the pixels are accumulated, the calculated amount becomes greater than the actual amount of the filamentous microorganisms. When the difference between the luminance of the microorganisms and that of the background is small, optical nonuniformity occurs because the background luminance by an optical system cannot be made completely uniform. Accordingly, it is difficult to detect only the microorganisms.

SUMMARY OF THE INVENTION

It is therefore an object of the present invention to provide an apparatus for measuring the concentration of filamentous microorganisms which can always measure accurately the amount of filamentous microorganisms per unit volume, i.e., the concentration thereof, irrespective of their thickness.

It is another object of the present invention to provide an apparatus for accurately measuring the concentration of filamentous microorganisms by removing measurement errors resulting from illumination nonuniformity, and the like.

One of the characterizing features of the present invention resides in that after a gray image of filamentous microorganisms is binarized, this binarized image is subjected to thinning treatment so that the thickness of the filamentary portions corresponds to one pixel.

Another characterizing feature of the present invention lies in that background image before sampling of the microorganisms is subtracted from image information after sampling to obtain the image information on the microorganisms alone, and an arbitrary luminance level is set for the luminance information that the image information has so as to extract the number of pixels corresponding to the intended microorganisms.

Still another characterizing feature of the present invention lies in that portions having a large luminance difference are selectively extracted from the original image of the microorganisms that is photographed and enhanced in order to clarify the filamentous microorganisms, a thinning treatment is then effected to establish correspondence of pixels on the 1:1 basis and thereafter contraction and expansion are made.

BRIEF DESCRIPTION OF THE DRAWINGS

FIG. 22 shows the construction of the embodiment described above;

DESCRIPTION OF THE PREFERRED EMBODIMENTS

Hereinafter, some preferred embodiments of the invention will be described with reference to the accompanying drawings.

Figure 1:
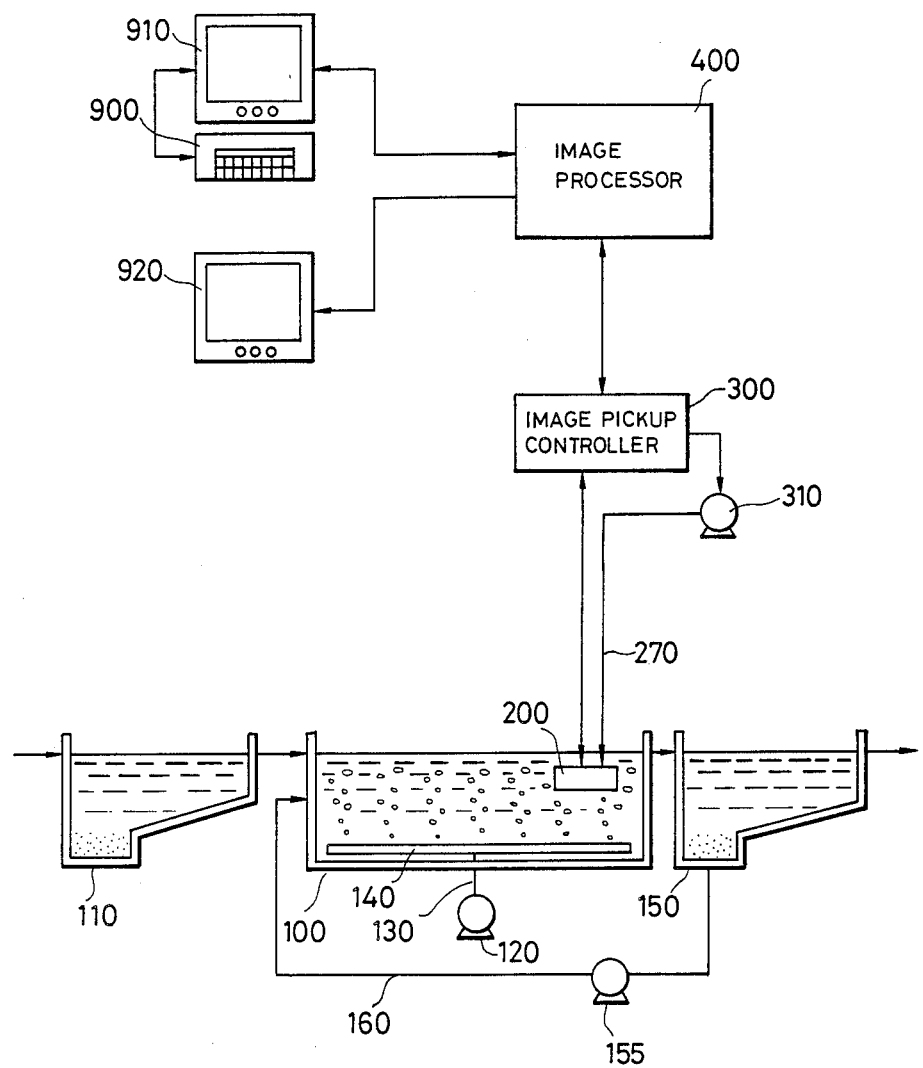
FIG. 1 is a schematic view showing the overall construction of an apparatus for measuring the concentration of microorganisms in an aeration tank of a sewage treatment plant as an example of the application of the present invention.

FIG. 1 shows an embodiment of the invention which is applied to a sewage treatment process.

Figure 2:
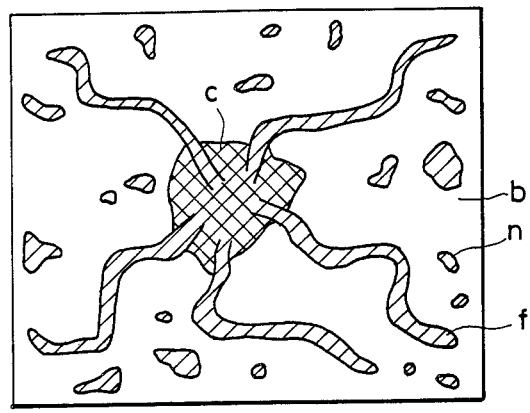
FIG. 2 is a schematic view showing one example of a microorganism image taken by an image pickup device contained in the measuring apparatus described above.

In FIG. 1, a supernatant (sewage) of a first sedimentation basin 110 and a return sludge (microorganisms) from a sludge recirculating pipe 160 flow into an aeration tank 100. On the other hand, air is blown by a blower 120 through an air duct 130 and is supplied into the aeration tank 100 from a diffuser 140. The return sludge and the sewage supplied into the aeration tank 100 are stirred and mixed. The return sludge or activated sludge consists of flocs formed by flocculation of the microorganisms and having a particle diameter of from about 0.1 mm to 1.0 mm, and contains dozens of kinds of microorganisms. They can be classified broadly into zoogleal microorganisms f (hereinafter called "floc microorganisms") c and filamentous microorganisms f as shown in FIG. 2. The activated sludge absorbs oxygen in the supplied air and decomposes organic matters in the sewage into a carbonic acid gas and water. Part of the organic matters is assigned to the increase of microorganism concentration of the activated sludge. The mixed solution of the activated sludge and the sewage is introduced into a second (final) sedimentation basin 150, where the activated sludge is subject to gravity sedimentation. Generally, the supernatant is chlorinated and is then discharged. On the other hand, the sedimented sludge is returned to the aeration tank 100 as the return sludge from the second sedimentation basin 150 through the sludge recirculating pipe 160 by a pump 155.

An image pickup device 200 is dipped and disposed in the liquid in the aeration tank 100 and has a function of obtaining an enlarged image of the microorganisms in the aeration tank 100. An image pickup controller 300 controls the timing of image pickup scanning of the image pickup device 200 (horizontal and vertical sync) and illumination intensity, and at the same time, transfers the enlarged image (gray image) of the mixed solution (containing water and the microorganisms) obtained by the image pickup device 200 to an image processor 400. The image processor 400 processes the gray image, recognizes the filamentous microorganisms in the image and measures their amount.

A keyboard 900 is used for inputting numeric values such as parameters of image processing used for the image processor 400. A console display 910 displays the numeric values inputted by the keyboard 900 and the amount of the filamentous microorganisms in terms of numerical values. A monitor television 920 displays the image of the image pickup device 200 and the process and result of image processing.

Figure 3:
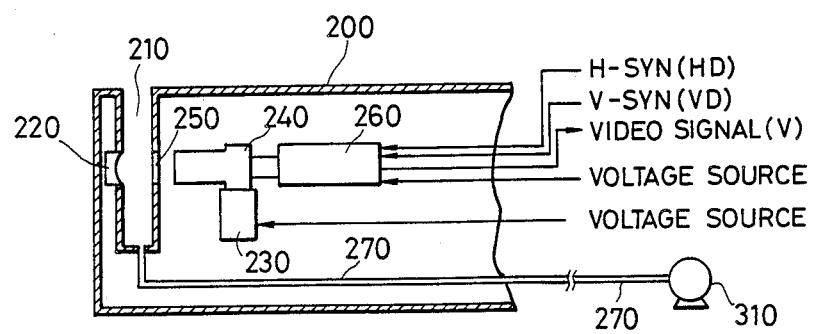
FIG. 3 is a schematic view showing an example of the image pickup device described above.

FIG. 3 shows in detail the construction of the image pickup device 200. The image pickup device 200 sequentially picks up the images of the solution containing the activated sludge inside the aeration tank 100, and an underwater camera having an optical magnification system, for example, can be used as the image pickup device 200. The image pickup device 200 shown in the drawing is directly dipped into the solution, and has a sample chamber 210 at its front head portion. The mixed solution of the aeration tank 100 directly flows through this sample chamber 210.

The image pickup device 200 incorporates therein an optical magnification portion 240, an image pickup portion 260 and an illumination portion 230. Electric power is supplied from outside to the illumination portion 230, and the light emitted from this portion is incident into the optical magnification portion 240 and after its travelling path is changed by a half mirror or the like, not shown in the drawing, the light passes through a cell window 250, is reflected by a mirror 220 opposing the window 250 and illuminates the mixed solution inside the sample chamber 210. The principle of magnification of ordinary microscopes can be applied to the optical magnification portion 240, which has an objective lens and an ocular. The image of the microorganisms in the sample chamber 210 magnified by the optical magnification portion 240 is converted to an electric signal by the image pickup portion 260.

An ordinary industrial television camera (hereinafter called "ITV") can be used as the image pickup portion 260. It has matrix-like image pickup elements (not shown in the drawing) on its light receiving surface, receives vertical sync signals VD and horizontal sync signals HD and are scanned by them. These sync signals VD, HD are supplied from the image pickup controller 300. The image pickup element outputs a video signal having a varying output voltage in accordance with the luminance of the light received. The video signal from ITV 260 is sent to the image pickup controller 300. Incidentally, it is possible to use a device which samples batchwise the mixed solution and observes the sampled solution by the use of a microscope and ITV as the image pickup device 200.

The image pickup device 200 described above is controlled by the image pickup controller 300. The image pickup controller 300 controls the illumination portion 230 and ITV 260, and controls the intensity of illumination of the illumination portion 230, whenever necessary. The image pickup controller 300 controls the frequency of air-blows and duration of air-blow supplied by the compressor 310 into the sample chamber 210 through the air duct 270. Ordinarily, the air is blown with frequency of once per 5 seconds to 20 minutes and the duration of each air-blow is from 2 to 30 seconds. The frequency of air-blows and the duration of air-blow can be changed in accordance with the degree of contamination of the observation window 250 and in the sample chamber 210.

As described above, the image pickup controller 300 controls the image pickup device 200, receives the analog video signal of the gray image sent from ITV 260 and sends it to the image processor 400.

Figure 4:
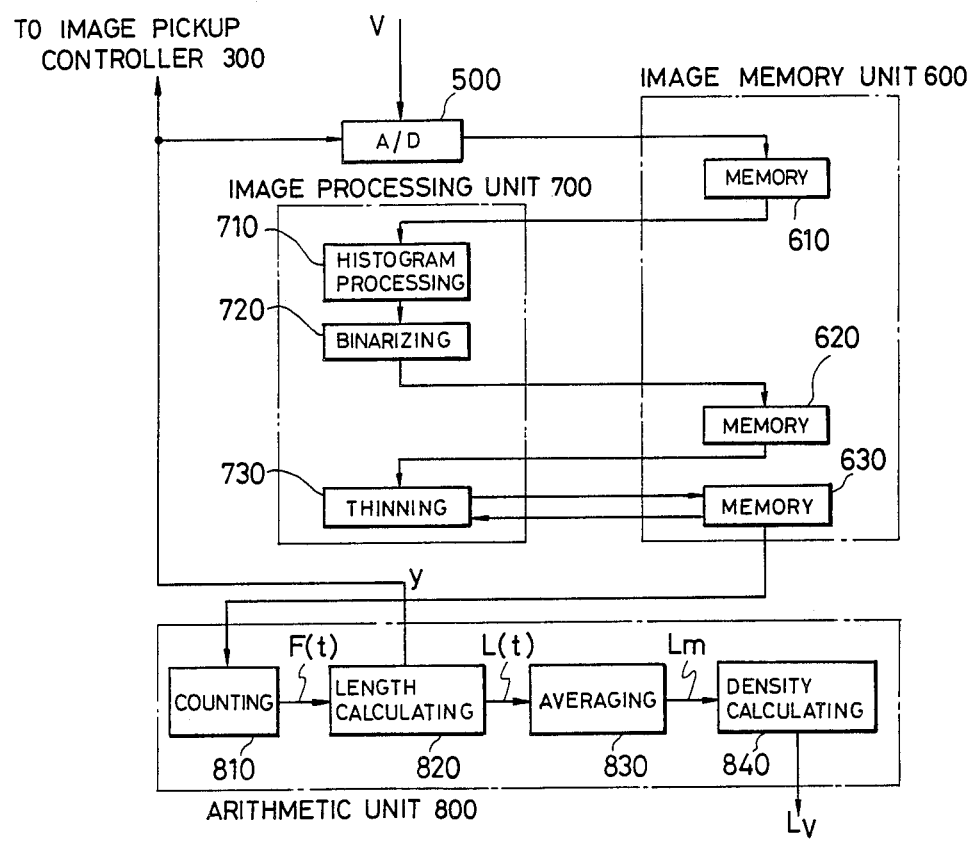
FIG. 4 is a block diagram showing the construction of an image processor contained in the measuring apparatus described above, in one embodiment of the present invention.

FIG. 4 shows in detail the construction of the image processor 400.

In FIG. 4, the image processor 400 consists of an A/D convertor 500, an image memory unit 600, an image processing unit 700 and an arithmetic unit 800. The image memory unit 600 consists of a memory 610 for the gray image and two memories 620 and 630 for binary data. An image processing unit 700 recognizes the filamentous microorganisms from the gray image and consists of a histogram processing means 710, binarizing means 720 and thinning means 730. The arithmetic unit 800 calculates the amount of the filamentous microorganisms recognized by means of the image processing unit 700 and consists of a filament counting means 810, filament-length calculating means 820, average length calculating means 830 and concentration calculating means 840.

In the construction described above, the A/D convertor 500 converts the analog video signal to a digital signal. The brightness of each pixel on a picture is converted to a digital value by this A/D convertor 500. The digital value has 128 levels, for example. The image memory unit 610 stores all the digital signals (gray image information of the mixed solution) of the brightness corresponding to each pixel. The frequency of A/D conversion of the video signal and storage of the gray image information in the image memory unit 610 are the same as the frequency of airblows into the sample chamber 210. In other words, when the existing mixed solution is replaced by a fresh mixed solution by the air blow into the sample chamber 210 and settles, the gray image is stored in the image memory unit 610. In this manner, the amount of the filamentous microorganisms is calculated by image processing on the basis of the gray image information stored in the image memory unit 610. Incidentally, the amount of the filamentous microorganisms can be calculated more accurately by conducting a later described image enhancement processing for the gray image information stored in the image memory unit 610 before calculation of the amount of microorganisms is made, though its procedure in detail is hereby omitted.

Figure 5:
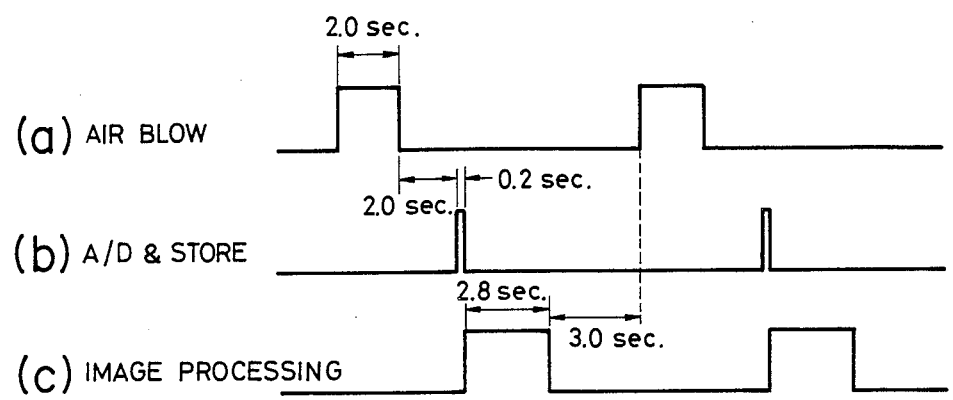
FIG. 5 is a time chart useful for explaining the operation timing of the measuring apparatus described above.

FIGS. 5(a) to 5(c) are timing charts showing the timing of the air-blow, the A/D conversion and storage of the gray image and the image processing. FIG. 5 shows the case where one cycle of these operations is conducted in ten seconds. As shown in FIG. 5(a), each air-blow is effected for 2.0 seconds, and then an interval of 2.0 seconds is inserted until the fresh mixed solution replaced by the air blow settles in the sample chamber 210. The A/D conversion of the video signal from the image pickup device 200 and the storage of the converted image information in the image memory unit 610 are effected in the subsequent 0.2 seconds. In subsequent 2.8 seconds, image processing is effected in the following way.

Next, the image processing operation in the image processing unit 700 will be explained.

Figure 6:
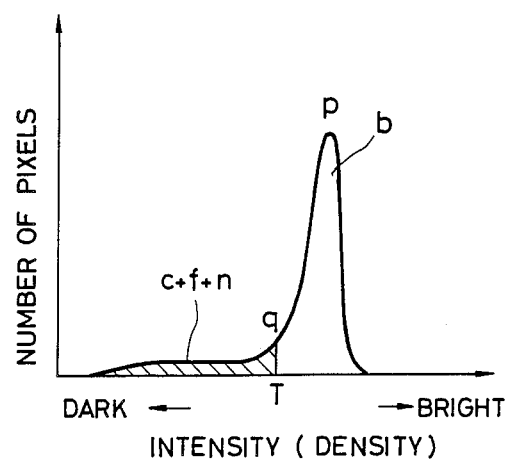
FIG. 6 shows an example of hystograms of the microorganism image (gray image) that is taken.

The histogram processing means 710 calculates the histogram, that is, the density frequency distribution, of the variable-density image information stored in the image memory unit 610. The histogram is a distribution characteristic diagram representing how many pixels of a certain density (intensity) exist. As shown in FIG. 6, the density (intensity) is plotted on the abscissa while the frequency (number of pixels) is plotted on the ordinate. The gray image of the image memory unit 610 contains a light background (water) b, the floc microorganisms c darker than the former, the filamentous microorganisms f and noise n, as shown in FIG. 2. The histogram of the gray image is divided into a portion corresponding to the light background (water) b and a portion (c+f+n) corresponding to the floc microorganisms c, the filamentous microorganisms b and the noise c, as shown in FIG. 6.

The binarizing means 720 determines a threshold value T of binarization on the basis of the histogram of the gray image obtained by the histogram processing means 710 and binarizes the gray image having various intensity (e.g. 128 tones) into black and white. For instance, the pixel whose intensity value is greater than the threshold value T is set to white ("1" level) and the pixel whose intensity value is smaller than the threshold value T is set to black ("0" level). The threshold value T is set to a value smaller by a predetermined value from the peak p of the background portion b or to an inflection point q shown in FIG. 6.

Figure 7:
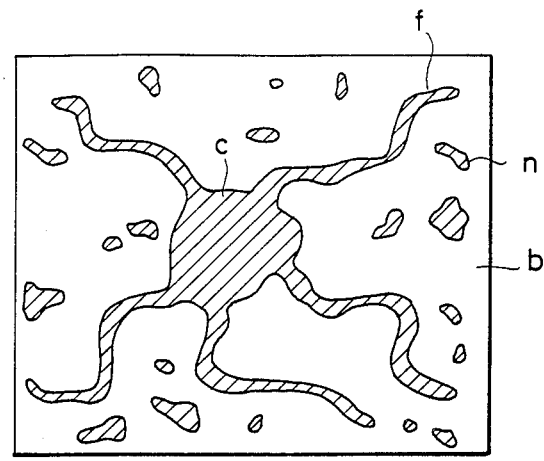
FIG. 7 shows a binarized image obtained by the binarizing treatment of the microorganism image taken.

FIG. 7 shows an example of the binarized image after the threshold value T is selected in the manner described above. In FIG. 7, the background b is white ("1" level) while the floc microorganisms c, the filamentous microorganisms f and the noise n are black ("0" level). The "0" level is represented by hatching. The resulting binarized image is stored in the image memory unit 620.

The binarized image signal in the image memory unit 620 is applied to the thinning means 730. This thinning means 730 thins the binarized image in the image memory unit 620 into a plurality of thin lines and extracts the filamentous microorganisms. As depicted in FIG. 2, the filamentous microorganisms f constitute the backbone of the floc microorganisms c and are contained in the latter, too. The filamentous microorganisms f contained in the floc microorganisms c overlap with the latter, and hence the binarized image shown in FIG. 7 contains both the filamentous microorganisms f and the floc microorganisms c. Thinning processing is conducted several times in order to extract only the filamentous microorganisms f from the binarized image shown in FIG. 7.

Figure 8:
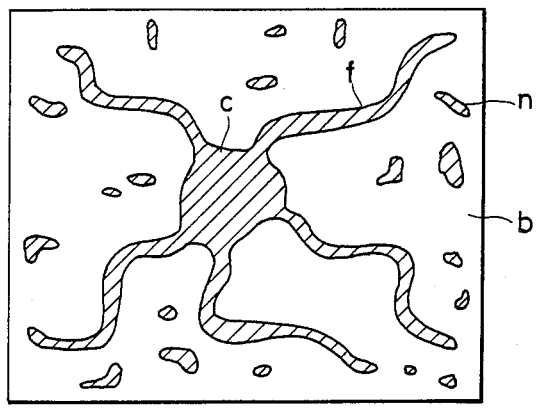
FIGS. 8 and 9 show the microorganism images (binarized images) after thinning treatment of the binarized image described above.

When thinning of the binarized image of FIG. 7 is made only once, the resulting image is such as shown in FIG. 8. Pixels are cut off one by one from the profile of the image of the filamentous microorganisms f and the floc microorganisms (the hatching portion in FIG. 7) by thinning processing. In this case, the pixel is not cut off from the portion where only pixel exists. If three pixels exist, for example, one each pixel is cut off from both sides and the thickness has only one pixel. If two pixels exist, only one pixel on one side is cut off, so that the thickness comes to have only one pixel.

The thinning processing described above reduces the thickness of the filamentous microorganisms having 1 to 3 pixels to have one pixel and those having four or more pixels to have two or more pixels. The binarized image after the first thinning processing is stored once in the image memory unit 630. The binarized image is further subjected to the thinning processing a plurality of times in order to reduce the thickness of the microorganisms having two or more pixels after the first thinning processing. These procedures are repeated until the thickness of the filamentous microorganisms becomes one pixel.

Figure 9:
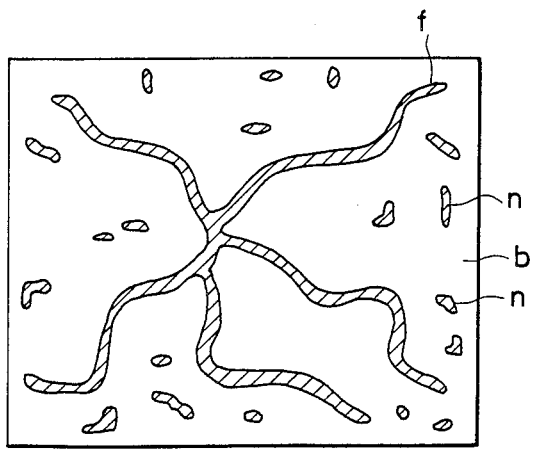

In this case, the filamentous microorganisms f which overlap with the floc microorganisms c cannot be cut off by more than one pixel by the thinning processing, so that the image becomes eventually such as shown in FIG. 9. In this manner, even when the thickness of the filamentous microorganisms is two to three pixels, all of them can be extracted as one pixel. The number of repetition of thinning processing can be determined by the number of pixels of the diameter of the floc microorganisms. If the diameter of the floc microorganisms is 50 pixels, for example, the thickness can be reduced to one pixel by effecting thinning processing 25 times. Since the thinning processing does not reduce the object below one pixel, the number of repetition may be more than 25 times. In order to avoid unnecessary repetition, however, the binarized images before and after the thinning processing are compared to check whether or not they are the same and if they are found to be the same (or the image which cannot be thinned any longer), the thinning processing is terminated. Incidentally, the thinning processing described above is effected when the binarized image data of the image memory unit 620 is updated.

Turning back to FIG. 4, the operation of the arithmetic unit 800 for calculating the concentration of the filamentous microorganisms from the number of pixels will be explained.

The counting means 810 counts the number of pixels of the filamentous microorganisms extracted as having the thickness of one pixel from the gray image at a time t. More definitely, it counts the number of pixels of only the hatched portion (the pixels assuming the "0" level value) in the resulting binarized image in FIG. 9. This counted number of pixels is called F(t). The length calculating means 820 calculates the overall length L(t) of all of the filamentous microorganisms from the counted number of pixels F(t) in accordance with the following equation:

$$L(t) = A \cdot F(t) - B \tag{1}$$

where A and B are coefficients.

Figure 10:
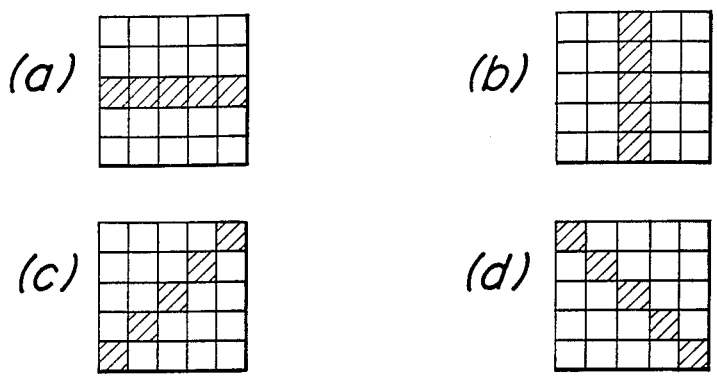
FIG. 10 is an explanatory view useful for explaining the alignment of pixels in the binarized image.

When, for example, the length of one side of one pixel corresponds to 10 μm (0.01 mm), the coefficient A is 0.01. When the filamentous microorganisms are aligned either horizontally or vertically as shown in FIG. 10(a) or (b), the coefficient A is 0.01 but when they are aligned upwardly rightwards or upwardly leftwards at an angle of inclination of 45°, however, the value of the coefficient A is $0.02 \times \sqrt{2} = 0.014$. When the filamentous microorganisms are uniformly distributed horizontally, vertically and upwardly rightwards or upwardly leftwards at 45°, the number of the horizontal and vertical pixels is believed to be the same as the number of upwardly rightward or upwardly leftward pixels at 45°. In such a case, the A value is a mean value of 0.01 and 0.014 ($=0.01 \times \sqrt{2}$), that is, 0.012.

The coefficient B is to correct the error. In other words, the binarized image extracted by the thinning processing contains also small floc microorganisms (whose amount is small) not containing the filamentous microorganisms as represented by n in FIG. 9 and this results in the measurement error. It is therefore preferred to remove the value resulting from the microorganisms n from the length of the filamentous microorganisms determined from the counted value F(t). The coefficient B is a value resulting from the microorganisms n, and the method of counting it will be described later in detail.

After the length L(t) of the filamentous microorganisms is calculated for the gray image of one image plane in the manner described above, the filament-length calculating means 820 sends a signal y to the A/D convertor 500 and to the image pickup controller 300 so that a second sampling and calculation can be executed.

Namely, the image pickup controller 300 controls the compressor 310, supplies air into the sample chamber 210 through the air duct 270 and cleans and exchanges the sample (mixed solution). Next, the gray image is subjected to A/D conversion in the same way as described above and the converted image is once again stored in the image memory unit 610 at a time t+h (where h is a sampling period). Then, the same procedures described above are repeated in the image memory unit 600 and the image processing unit 700. The length of the filamentous microorganisms obtained by the filament-length calculating means 820 in this second processing is hereby called L(t+h). In this manner, the filament-length calculating means 820 calculates sequentially the lengths of the filamentous microorganisms, i.e., L(t), L(t+h), L(t+2h), ..., L(t+Kh), of the image at the time t, t+h, t+2h, ..., t+Kh, for each sampling time h.

The averaging means 830 calculates the average length Lm of the filamentous microorganisms per one picture surface from L(t), L(t+h), L(t+2h), ..., L(t+Kh) outputted from the filament-length calculating means 820 in accordance with the following equation:

$$Lm = \left( \sum_{i=0}^{K} L(t + ih) \right) / K \quad (2)$$

Here, K is the number of image planes whose images are picked up, and this value is determined in accordance with the accuracy required for the judgement of microbial growth.

Upon receiving the signal Lm from the averaging means 830, the density calculating means 840 calculates the amount Lv of the filamentous microorganisms per unit volume (that is, the concentration of the filamentous microorganisms) in accordance with the following equation:

$$Lv = Lm/v \quad (3)$$

where $v$ is the volume of the mixed solution whose image is picked up.

The amount of the filamentous microorganisms per unit volume can be obtained by the processing described above. In this embodiment binarization is made on the basis of the histogram of the gray image and after the binarized image is thinned, the amount of the filamentous microorganisms is calculated. Therefore, the amount of the filamentous microorganisms contained in the floc microorganisms can be measured accurately.

In the embodiment described above, all of the image processor unit 700, the image memory unit 600 and the arithmetic unit 800 are respectively composed of discrete means in order to have the present invention more easily understood. In practice, an ordinary microprocessor which is programmed in such a manner as to exhibit the function of each of the units described above is employed as the image processor 400. Such a program can be prepared easily by those skilled in the art in light of the description of the embodiment given above.

Figure 11:
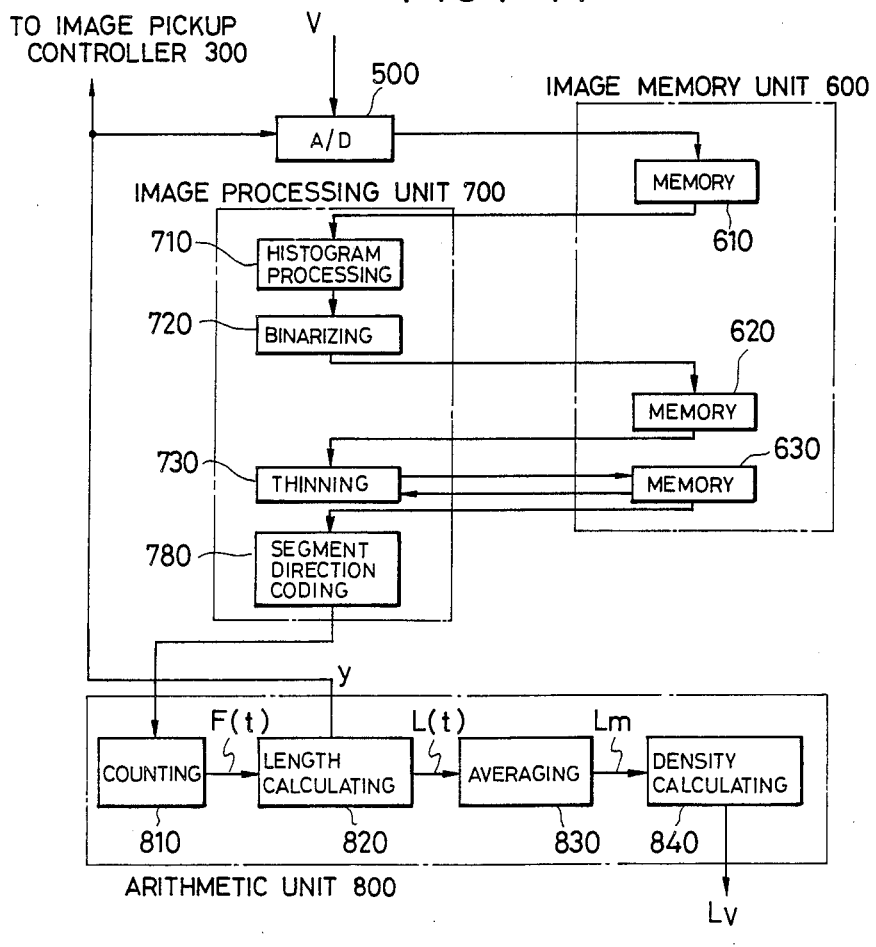
FIG. 11 is a block diagram showing the construction of an image processor in another embodiment of the present invention.

FIG. 11 shows the image processor in accordance with another embodiment of the present invention.

This embodiment is constituted by adding segment direction code processing means 780 to the embodiment shown in FIG. 4, in order to accurately determine the amount while taking the connecting direction of the pixels of the filamentous microorganisms into consideration. In other words, even if the number of the counted pixels is the same, the calculated amount is somewhat different from the actual amount of the filamentous microorganisms depending upon the connecting direction of these pixels (see FIGS. 10(a) to 10(d)). The embodiment shown in FIG. 4 assumes that the connecting directions of the pixels are distributed uniformly, and proposes that the coefficient A of the formula (1) for calculating L(t) is set to an average value. The embodiment shown in FIG. 11 accomplishes a higher level of measurement accuracy by taking the distribution state of the connecting directions into consideration.

Figure 12:
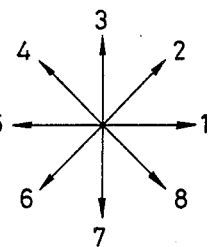
FIG. 12 is an explanatory view useful for explaining the direction code that represents the combining directions of the pixels and is used in the embodiment of the invention shown in FIG. 11.

In FIG. 11, the segment direction code processing means 780 receives the signal from the image memory unit 630 and calculates the direction code of line segment of the pixel of the filamentous microorganisms. When 3×3 pixels such as shown in FIG. 12(a) are considered, the direction code of line segment represents, in terms of code numbers shown in FIG. 12(b), in which direction a specific pixel is connected from the pixel at the center 9. To determine the direction code of line segment, the directions of the filamentous microorganisms are sequentially examined to count which code number of the segment direction code each pixel corresponds.

As a result, the total number of pixels corresponding to the respective code numbers can be counted. The filament counting means 810 receives the signal from the segment direction code processing means 780 and counts the number of pixels $F_1(t)$ whose code numbers are odd-numbered and the number of pixels $F_2(t)$ whose code numbers are even-numbered. Upon receiving the signals of $F_1(t)$ and $F_2(t)$, the filament-length calculating means 820 calculates the length L(t) of the filamentous microorganisms. When the segment direction code is odd-numbered, the value of the coefficient A of $F_1(t)$ is set to 0.01, and when it is even-numbered, the value of the coefficient A is set to 0.014. In other words, the filament-length calculation process executes the following calculation:

$$L(t) = 0.01 \cdot F_1(t) + 0.014 \cdot F_2(t) - B \quad (4)$$

Upon receiving the signal L(t), the averaging means 830 calculates the average length Lm of the filamentous microorganisms per unit image plane. Then, the arithmetic unit 800 executes the same operation as that of FIG. 4 and determines the length $L_v$ of the filamentous microorganisms per unit volume, i.e., the concentration thereof.

The calculation process described above can accurately determine the amount in whichever directions the pixels of the filamentous microorganisms are connected. In other words, the operation which is the same as the manual tracing operation of the filamentous microorganisms by people using a curvometer can be accomplished.

In the manner described above, the embodiment shown in FIG. 11 can provide substantially the same effect as that of the embodiment shown in FIG. 4. Moreover, since the concentration of the filamentous microorganisms is determined while the connecting directions of the pixels are taken into account, the length can be measured accurately even when the filamentous microorganisms are connected in horizontal, vertical and slanting directions.

Figure 13:
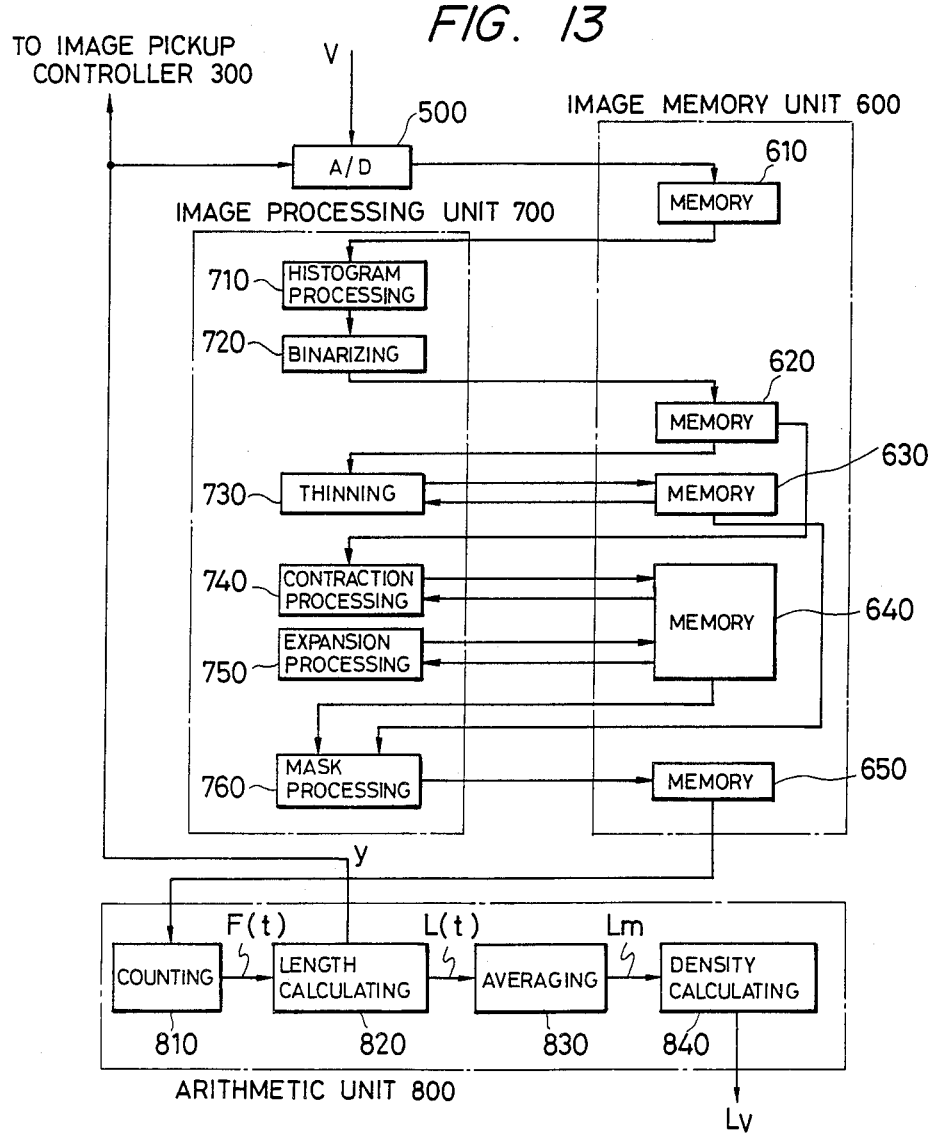
FIG. 13 is a block diagram showing the construction of the image processor in still another embodiment of the present invention.

FIG. 13 shows still another embodiment of the present invention.

The embodiment shown in FIG. 13 is adapted to extract only the filamentous microorganisms that project from the floc microorganisms.

The embodiment shown in FIG. 13 is constituted by adding contraction processing means 740, expansion processing means 750 and mask processing means 760 to the embodiment shown in FIG. 4.

First, the processing by the contraction processing means 740 and the expansion processing means 750 will be explained. The contraction processing means 740 removes the filamentous microorganisms and noises having a thickness of two pixels or less by one contraction processing. Next, only the floc microorganisms that have been contracted by the contraction processing means are expanded to their orginal size by the expansion processing means 750.

The contraction processing means 740 takes the binarized image (shown in FIG. 7) stored in the image memory unit 620 therefrom and contracts and then stores the binarized image in the image memory unit 640. This contraction processing cuts off the profile of the "0" level portion represented by hatching pixel by pixel. Unlike the thinning processing, this contraction processing cuts off simply the pixels one by one from the profile, so that the filamentous microorganisms whose width corresponds to two pixels are cut off pixel by pixel from both sides of the profile and disappear. Thus, the filamentous microorganisms whose thickness corresponds to two pixels disappear by the first contraction processing and at the same time, pixels are also cut off one by one from the profile of the floc microorganisms.

Figure 14:
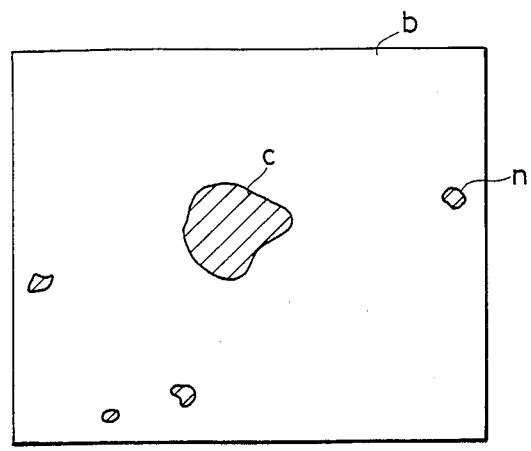
FIG. 14 shows a microorganism image (binarized image) obtained by contracting the binarized image shown in FIG. 7.

When the binarized image shown in FIG. 7 is once contracted in the manner described above, the resulting image becomes such as shown in FIG. 14. The contracted binarized image is again stored in the image memory unit 640. This contraction processing can substantially eliminate the filamentous microorganisms.

Figure 15:
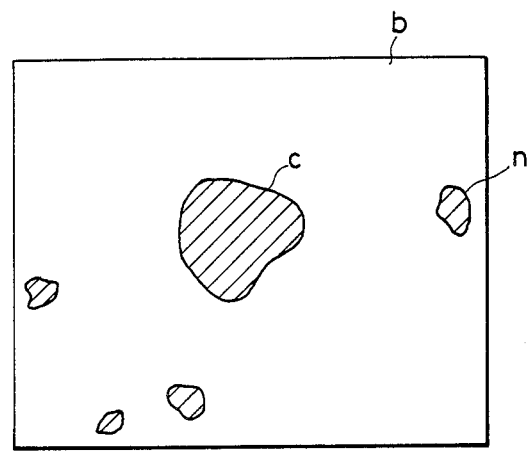
FIG. 15 shows a microorganism image (binarized image) obtained by expanding the contracted binarized image shown in FIG. 14.

Since the profile of the floc microorganisms is cut off pixel by pixel by the contraction processing, it must be restored to its original size. Therefore, the expansion processing 750 expands the signal of the image memory unit 640, that is, the binarized image shown in FIG. 15. In this expansion processing, pixels are added one by one to the surroundings of the "0" level portions represented by hatching. In other words, the pixels are added one by one to the profile of the floc microorganisms c of the image shown in FIG. 14. As a result, the image becomes such as shown in FIG. 15. Some noise n remains due to this operation but the floc microorganisms can be extracted. The result is stored once again in the image memory unit 640.

Figure 16:
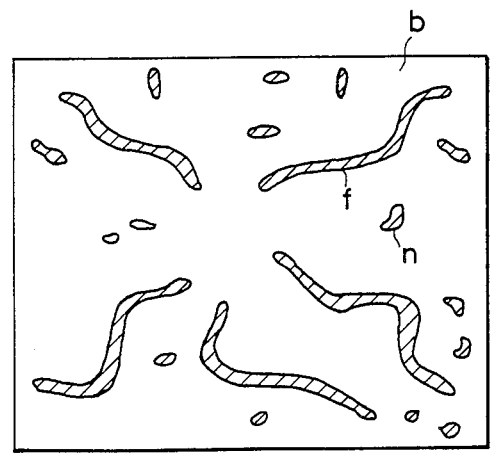
FIG. 16 shows a microorganism image (binarized image) obtained by masking treatment of the expanded binarized image shown in FIG. 15 for the binarized image shown in FIG. 9.

The mask processing means 760 extracts the length of the filamentous microorganisms projecting from the floc microorganisms on the basis of the binarized image (shown in FIG. 9) stored in the image memory unit 630 and the binarized image (shown in FIG. 15) stored in the image memory unit 640. More definitely, the portion of the floc microorganisms c (the value of the "0" level represented by hatching) is masked and extracts the filamentous microorganisms (at the white portion and having the value of the "1" level) other than the floc microorganisms c shown in FIG. 9. As a result of this mask processing, the filamentous microorganisms f such as shown in FIG. 16 can be extracted and are stored in the image memory unit 650. The operation which calculates the concentration Lv of the filamentous microorganisms from the binarized image (FIG. 16) stored in this memory unit 650 is the same as the operation described in the embodiment shown in FIG. 4. Additionally, it is of course possible to add the segment direction code processing means 780 of the embodiment shown in FIG. 11, though the means is not shown in FIG. 13.

As described above, the embodiment of FIG. 13 provides the effect substantially equal to that of the embodiment of FIG. 4, and moreover can extract only the filamentous microorganisms that have conventionally been the object of measurement with human eyes because the embodiment extracts only the filamentous microorganisms not contained in the floc microorganisms.

Figure 17:
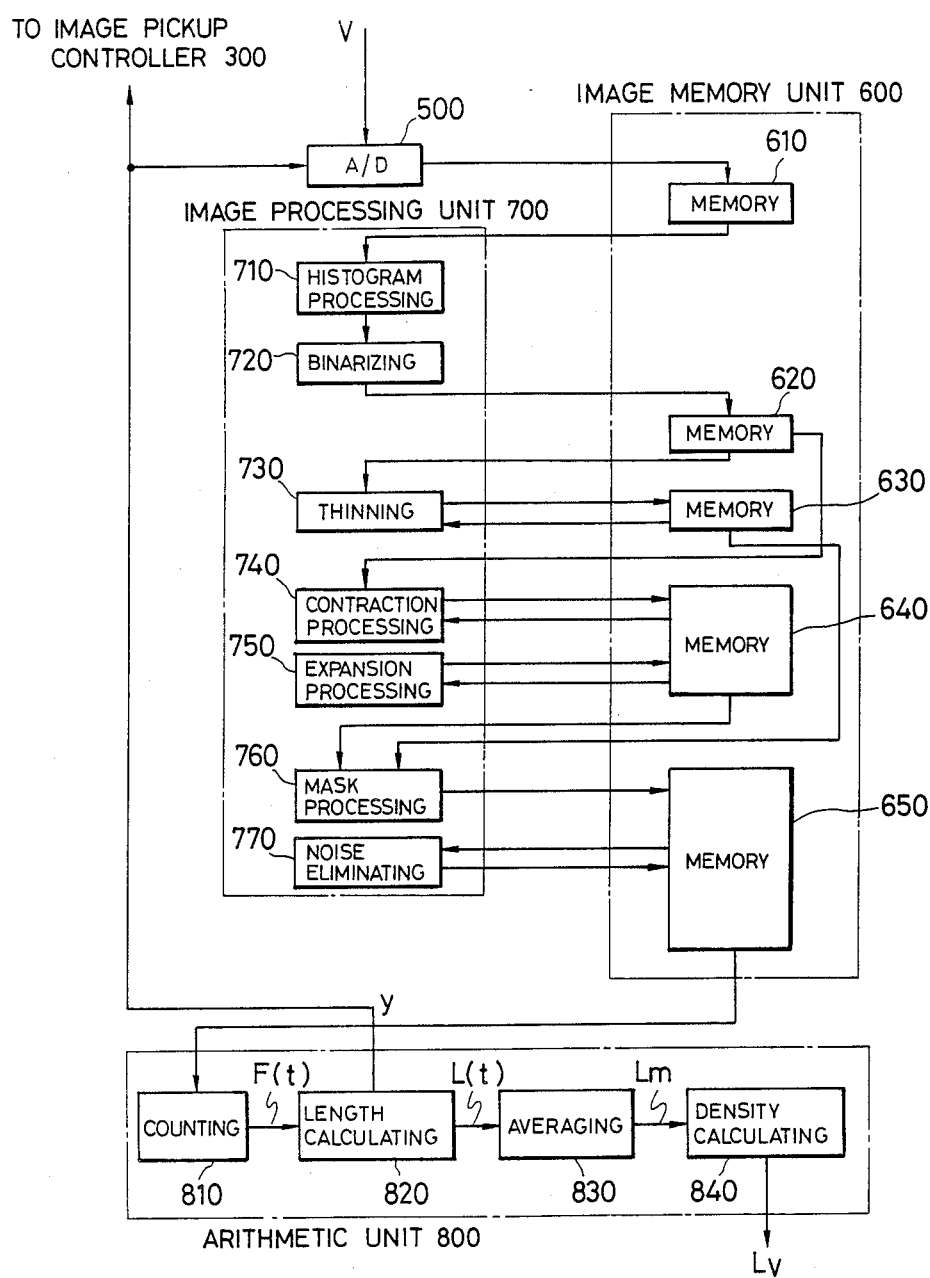
FIG. 17 is a block diagram showing the construction of the image processor in still another embodiment of the present invention.

FIG. 17 shows still another embodiment of the present invention.

The embodiment shown in FIG. 17 is directed to improve the accuracy of measurement of the length of the filamentous microorganisms, and is constituted by adding noise eliminating means 770 to the embodiment shown in FIG. 13. The noise eliminating means 770 eliminates the noise from the binarized image (shown in FIG. 16) stored in the image memory unit 650. This noise n results from individual microorganisms or small floc microorganisms that are left as lines in the thinning processing 730.

Figure 18:
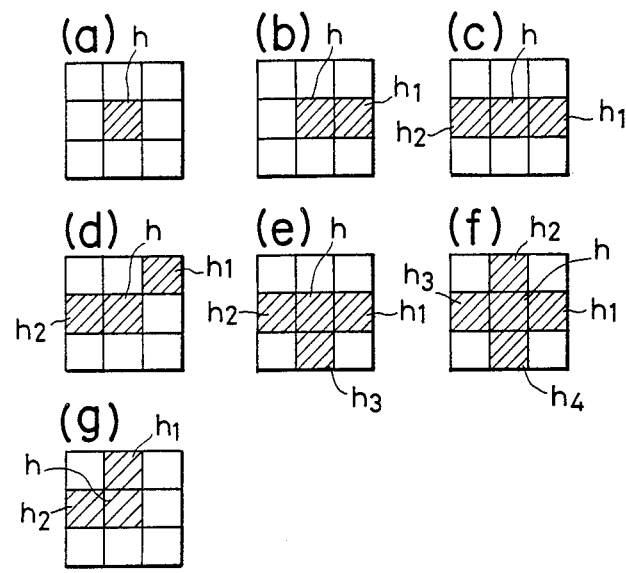
FIG. 18 is an explanatory view useful for explaining the principle of operation of the image processor shown in FIG. 17.

The noise eliminating means 770 eliminates the noise in the following way. The noise n left after thinning assumes patterns such as shown in FIG. 18(a) to (g). They are contained in a $3 \times 3$ pixel region. What is contained in a $4 \times 4$ pixel region is extracted as floc microorganisms and not counted as filamentous microorganisms. Therefore, such need not be considered to be noise. FIG. 18(a) shows the noise of one pixel h, and this noise is removed by extracting an independent one pixel h that exists in the binarized image (FIG. 17) of the image memory unit 650.

Next, when $h_1$, $h_2$, $h_3$ and $h_4$ in the patterns shown in FIGS. 18(b) to (g) are removed as the end points (as the pixels at the end points), the pixel h at the center remains. Since the pixel h at the center is an independent point, it is eliminated as the noise of one pixel.

Figure 19:
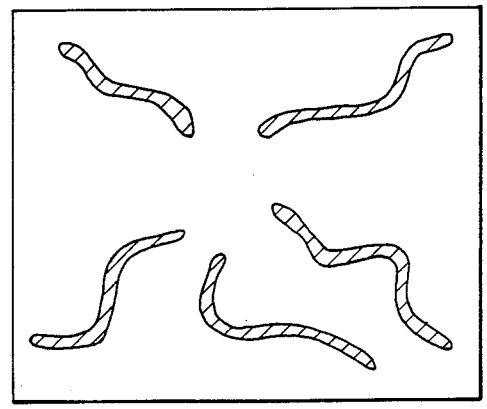
FIG. 19 shows a microorganism image (binarized image) obtained by the age processor shown in FIG. 17.

FIG. 19 shows the result of noise elimination after the procedures described above are effected by the noise eliminating means 770 to eliminate the noise n. Though FIG. 16 shows an example where the noise is small, a lot of fine dirt and microorganisms are contained actually in the mixed solution of the activated sludge. Accordingly, if such dirt and microorganisms are eliminated as the noise, the error can be reduced and hence the measurement accuracy can be improved effectively.

The method of calculating the amount Lv of the filamentous microorganisms per unit volume by the arithmetic unit 800 after it receives the binarized image (FIG. 19) of the image memory unit 650 is the same as the method described in the embodiment shown in FIG. 4.

The embodiment shown in FIG. 17 provides substantially the same effect as the embodiment shown in FIG. 4, but since the former eliminates the noise other than the filamentous microorganisms, it can accurately extract only the filamentous microorganisms.

Further, when the image of the microorganisms is taken by the image pickup device 200, an accurate measurement becomes difficult if any nonuniformity exists in the lighting. If a thinly elongated scratch or scratches exist on the window 250 of the image pickup device 200, for example, the scratch will be erroneously recognized as the filamentous microorganisms and an error will occur in the result of measurement. Therefore, an improved method which eliminates these problems and can measure more accurately the concentration of the filamentous microorganisms will be described next.

Figure 20A:
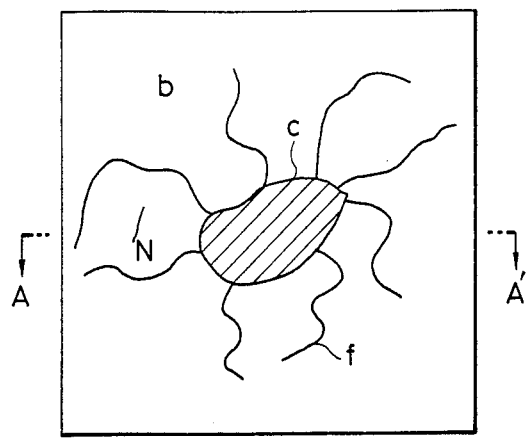
FIGS. 20(a), (b) and (c) and 21(a) and (b) are explanatory views useful for explaining the operation principle of still another embodiment of the present invention.
Figure 20B:
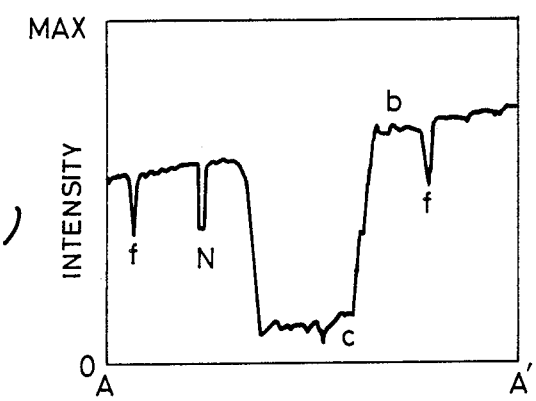

It will be assumed, for example, that the gray image such as shown in FIG. 20(a) is taken by the image pickup device 200. In the drawing, symbols b, c and f represent the background (water), the zoogleal (floc) microorganisms and filamentous microorganisms in the same way as in FIG. 2. Symbol N represents the image of the scratch on the window 250. It will also be assumed that non-uniformity of light exists in such a fashion that the intensity increases progressively from the left side to the right side of the drawing, though not shown in the drawing. FIG. 20(b) shows the intensity luminance distribution on the line A—A' in FIG. 20(a). In FIG. 20(b), MAX represents the maximum value of intensity. The background b exhibits a high intensity while the floc microorganisms f exhibits a low intensity. As shown in the drawing, the intensity of the background b has nonuniformity due to nonuniformity of the lighting, so that the intensity level of the filamentous microorganisms f becomes nonuniform, too. Since the intensity of the scratch N is analogous to that of the filamentous microorganisms, there is a high possibility that the scratch N is extracted as the filamentous microorganisms.

Figure 20C:
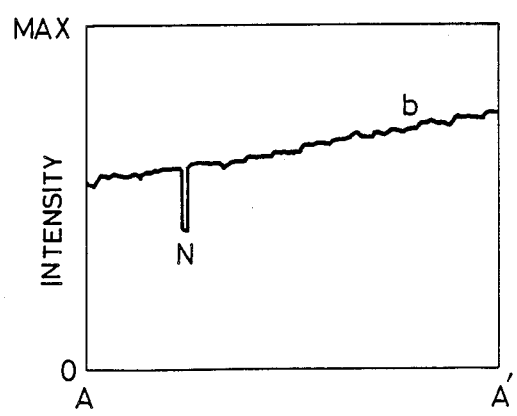

This embodiment conducts the following processing in order to solve the problems described above. First of all, the image of only the background b before the introduction of the mixed solution into the sample chamber 210 is taken. The intensity distribution of this image on the line A—A' in the same way as in FIG. 20(a) becomes such as shown in FIG. 20(c) due to the scratch N and the nonuniformity of lighting. The intensity signal of a (i,j) pixel of such an image is called W(i, j), and the intensity signal of the (i,j) pixel of the image taken after the introduction of the mixed solution is called S(i, j). Then, corrected intensity signal information C(i, j) can be obtained in accordance with the following equation:

$$C(i, j) = S(i, j) + [MAX - W(i, j)] \qquad (5)$$

Figure 21A:
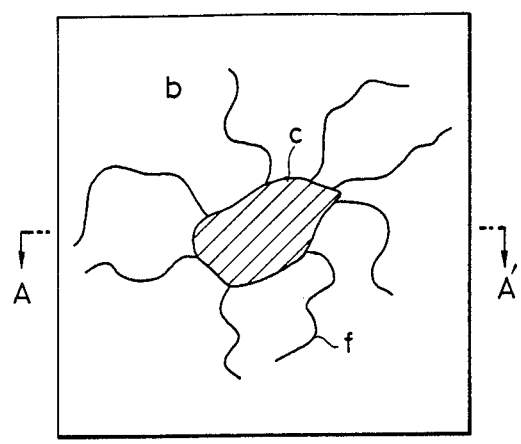
Figure 21B:
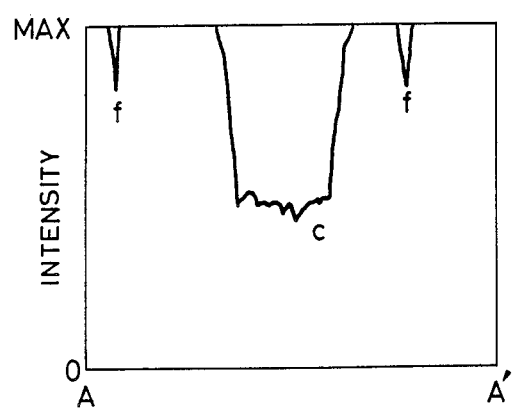

The intensity distribution of the resulting corrected intensity information C(i, j) on the line A—A' becomes such as shown in FIG. 21(a). The binarized image obtained from the corrected intensity information C(i, j) does not contain the image resulting from the scratch N as shown in FIG. 21(b), and the adverse influences of nonuniformity of lighting are also eliminated.

FIG. 22 shows still another embodiment of the invention which is based upon the concept described above. The drawing shows only the associated portions and the rest are the same as those of the embodiments described already. In addition, like reference numerals are used to identify like constituents as in the embodiments described already. In this embodiment, compensating means 705 and auxiliary memory 615 are added afresh. The image information W(i, j) taken before the start of measurement is converted to a digital signal by the A/D convertor 500 and is then stored in the auxiliary memory 615 through the image memory unit 610. Thereafter, the signal is retained in the memory 615. After the start of measurement, the contents of both memories 610 and 615 are led to the compensating means 705 whenever the image information S(i, j) is stored in the memory 610, where intensity compensation is conducted in accordance with equation (5) described above. The method of calculating the concentration of the filamentous microorganisms on the basis of the corrected intensity information C(i, j) is the same as the methods of the foregoing embodiments.

In accordance with the embodiment described above, the background intensity information devoid of any microorganisms is reduced from the microorganism intensity information, so that various problems occurring in the detection portion including the optical system such as nonuniformity of lighting, contamination, scratch, and the like, can be eliminated and the density of filamentous microorganisms can be measured more accurately.

Incidentally, if the intensity level of the background b is not constant as shown in FIG. 20(b), it is difficult to set the threshold value for discriminating the zoogleal (floc) microorganisms c from the filamentous microorganisms f to a constant value throughout the entire picture. Particularly when the threshold value is set to a considerably higher level in order to detect those filaments f which have considerably high intensity and a small difference of intensity from the background b, even part of the background b is detected, too, and this results in a great measurement error. To solve this problem, it is possible to employ a method which enhances the filamentous portion f of the image. Next, its embodiment will be explained with reference to FIGS. 23 to 27.

Figure 23:
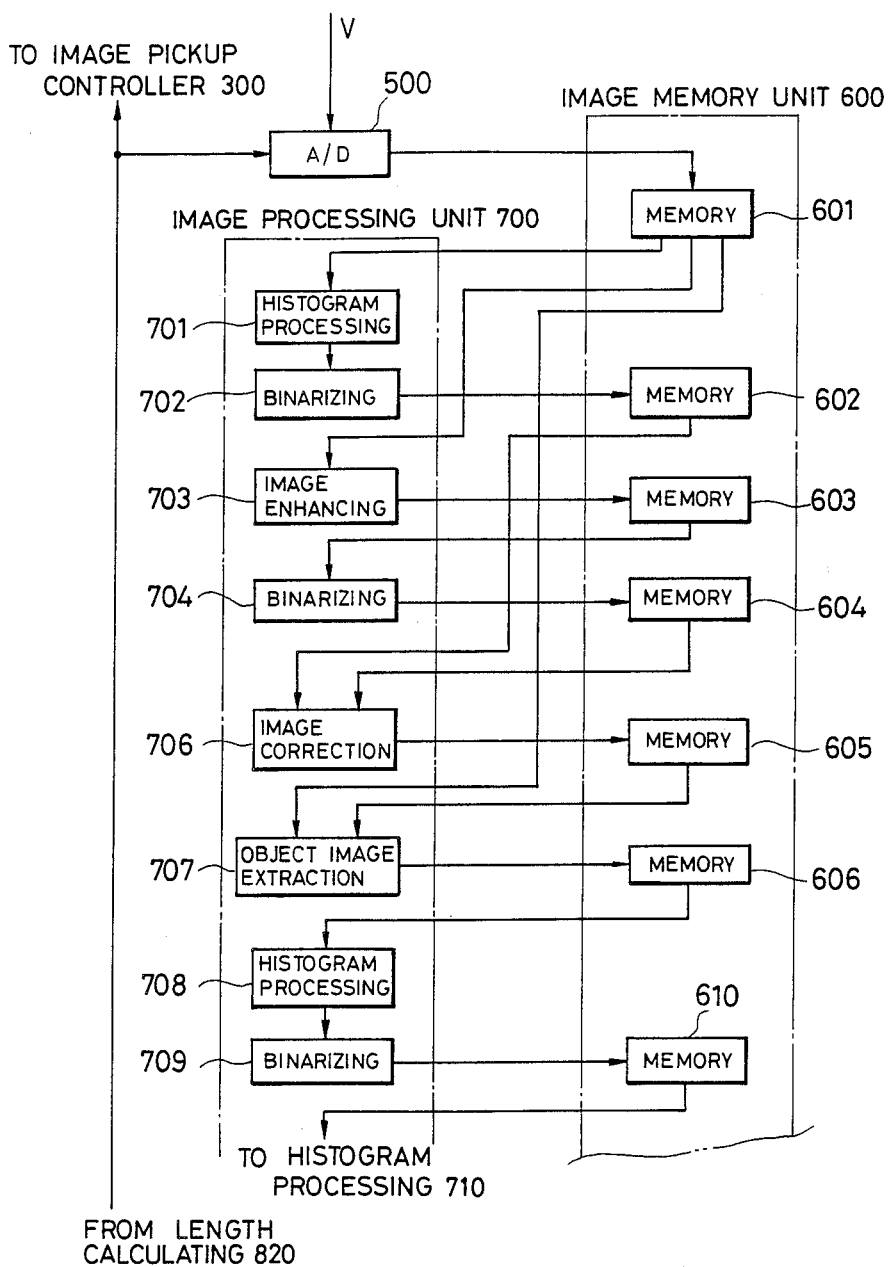
FIG. 23 is a block diagram showing the construction of an image processor in still another embodiment of the present invention.
Figure 24:
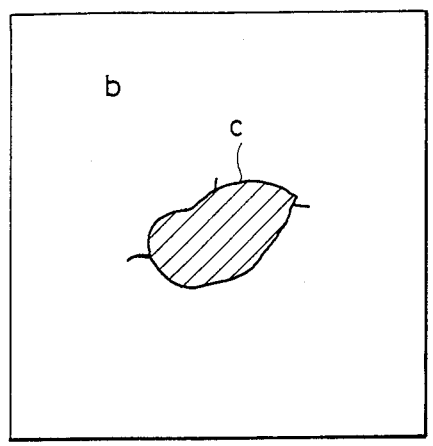
FIGS. 24, 26 and 27(a) and (b) are explanatory views useful for explaining the operation principle of the embodiment shown in FIG. 23.

FIG. 23 shows the construction of this embodiment, and only the associated principal portions are shown with the rest being the same as those of the foregoing embodiments. In addition, like reference numerals are used to identify like constituents as in the foregoing embodiments.

In the drawing, the video signal V obtained by picking up the image of the microorganisms such as shown in FIG. 20(a) is converted to a digital signal by the A/D convertor 500 and stored in the memory 601. The intensity information S(i, j) of the original image stored in the memory 601 is processed by the histogram processing means 701 to obtain the number of pixels (histogram) for each intensity throughout the entire picture. Furthermore, the original image S(i, j) is binarized by the binarizing means 702 in accordance with the following relation:

$$\left. \begin{array}{l} G_1(i, j) = 0 \text{ when } S(i, j) > SH_1 \\ G_1(i, j) = 1 \text{ when } S(i, j) \leq SH_1 \end{array} \right\} \qquad (6)$$

The threshold value $SH_1$ in this case is determined by the intensity peak value determined by the histogram processing means 701, and the determination method has already been described with reference to FIG. 6.

After the binarizing processing described above, the portion having a considerably lower intensity among the original image, that is, only the zoogleal (floc) microorganisms C, are extracted smaller in size than the original image and stored in the memory 602.

On the other hand, reference numeral 703 represents image enhancing means which effects image enhancement for the original image S(i, j) in accordance with the following equation:

$$S_1(i, j) = \Sigma S(i, j) \cdot W(i, j)/K_i \qquad (7)$$

Figure 25:
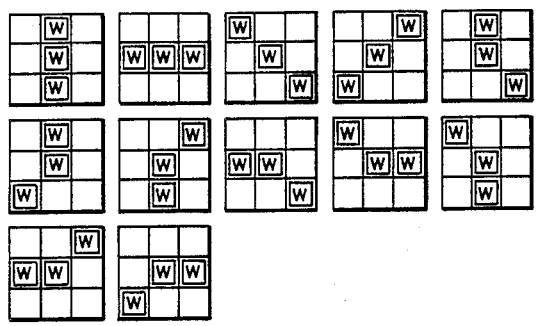
FIG. 25 is an explanatory view useful for explaining the operation principle of image enhancement used in the embodiment shown in FIG. 23.

The image enhancement assumes a group of 3×3 pixels, pays specific attention to one arbitrary pixel at the center and effects linear calculation with the surrounding eight pixels. In equation (7), W(i, j) is an enhancement coefficient, and FIG. 25 shows a definite method. The coefficients are expressed in three rows by three columns in order to enhance 12 kinds of lines having a width of one pixel. A positive value is assigned to each pixel with a square-framed W while a negative value is given to the other frames. In this case, each coefficient is set so that the sum of the enhancement coefficients becomes zero. In other words, the intensity of pixels at the portion devoid of any intensity change (flat intensity portion) is made zero.

In equation (7), Ki is a compensation coefficient which adjusts the enhanced image $S_1(i, j)$ to the intensity range so that it can be displayed by the image processor. This coefficient is set in consideration of the intensity difference between adjacent pixels and the enhancement coefficient. Due to this processing, the background portion b of the original image $S(i, j)$ having a small intensity difference is displayed in the enhanced image $S_1(i, j)$ at an intensity which is almost 0 while the extraction object portion having a large intensity difference, that is, the floc microorganisms c and the filamentous microorganisms f, is displayed at a high intensity. Since the enhancement coefficient is directed to the line, the portion among them which is the most enhanced is the filaments f. This enhanced image $S_1(i, j)$ is stored in the memory 603.

Reference numeral 704 represents the binarizing means, which binarizes the enhanced image $S_1(i, j)$ in accordance with the following formulas:

$$G_2(i, j) = 1 \text{ when } S_1(i, j) > SH_2, S_1(i, j) \leq -SH_2$$

$$G_2(i, j) = 0 \text{ when } -SH_2 < S_1(i, j) \leq SH_2 \tag{8}$$

This threshold value $SH_2$ is determined in accordance with the optical system of the image pickup device 200 and with ITV (sensitivity). This value must be determined on the trial-and-error basis because if it is too great, the filaments will get interrupted. However, there is no need to change the value unless the image pickup device 200 is changed, once the threshold value is determined.

Figure 26:
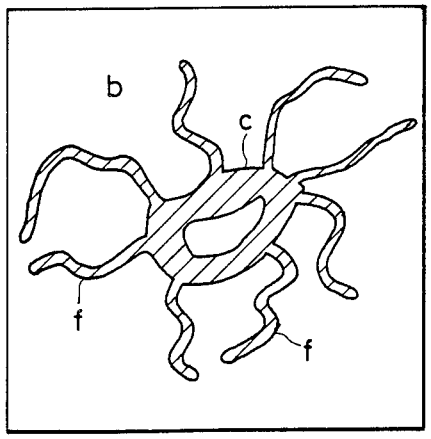

Since the background of the binarized image $G_2(i, j)$ in accordance with equation (8) which comes into contact with the microorganisms is enhanced as shown in FIG. 26, the binarized image $G_2(i, j)$ is detected as if the microorganisms of the original image $S(i, j)$ expanded, and a hole occurs inside the floc microorganisms c. This is because a portion having no intensity difference exists between adjacent pixels in the image of the floc microorganisms c of the original image $S(i, j)$ and is outputted by the image enhancing means 703 as the portion whose intensity is 0. This binarized image $G_2(i, j)$ is stored in the memory 604.

Reference numeral 706 represents image correction means. This means adds the pixels on the same coordinates of the binarized images $G_1(i, j)$ and $G_2(i, j)$ in accordance with the following equation (9) and sets the sum to 1 when the logical OR image $G_2'(i, j)$ is 1 or more and to 0 when the latter is less than 1. Thus, the hole range in the binarized image $G_2(i, j)$ becomes 1 and the microorganism portion and part of the background adjacent to the former are extracted. The logical OR image $G_2'(i, j)$ is stored in the memory 605.

$$G_2'(i, j) = G_1(i, j) + G_2(i, j)$$
$$G_2'(i, j) = 1 \text{ when } G_2'(i, j) \geq 1 \tag{9}$$
$$G_2'(i, j) = 0 \text{ when } G_2'(i, j) = 0$$

Reference numeral 707 represents object image extraction means, which extracts a region where the floc microorganisms c and the filamentous microorganisms exist in the original image $S(i, j)$ from the logical OR image $G_2'(i, j)$. Extraction is made in the following manner. The intensity of the pixel of the original image $S(i, j)$, which is on the same coordinates as the pixel which is outputted to 0 in the logical OR image $G_2'(i, j)$, is set to 0, while the intensity of the pixel of the original image $S(i, j)$ which is on the same coordinates as the pixel outputted to 1 in $G_2'(i, j)$ is not changed, and under this state, the intensity information of the original image is as such outputted. In other words, the calculation of the following equation is made.

$$S_2(i, j) = S(i, j) \text{ when } G_2'(i, j) = 1$$
$$S_2(i, j) = 0 \text{ when } G_2'(i, j) = 0 \tag{10}$$

Figure 27A:
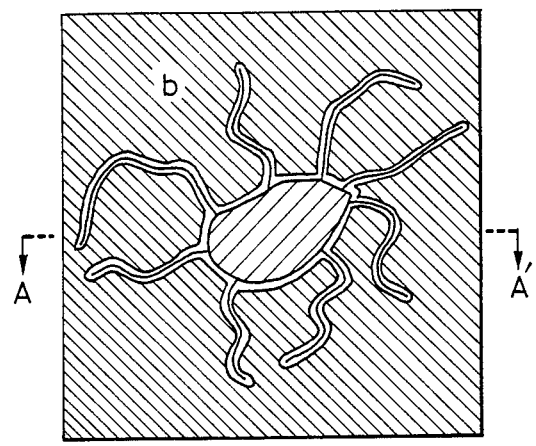
Figure 27B:
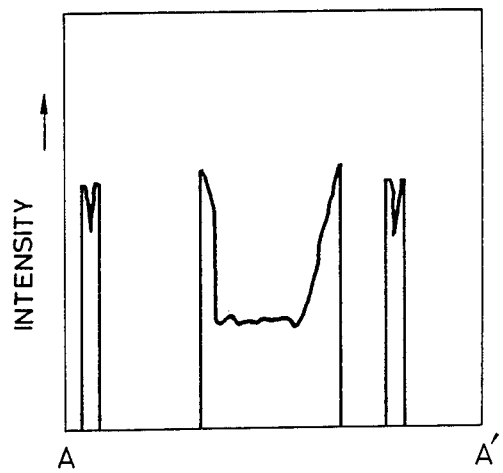

As shown in FIG. 27(a), this partial extracted image $S_2(i, j)$ takes the state where the image of the microorganisms of the original image is fitted to the expanded region shown in FIG. 26. When its intensity distribution is determined along the scanning position line A—A' in the same was as in FIG. 20(a), it becomes such as shown in FIG. 27(b) This partial extracted image $S_2(i, j)$ is stored in the memory 606.

Reference numeral 708 represents histogram processing means which obtains the histogram of the partial extracted image $S_2(i, j)$. In this histogram, the background portion extracted by the partial extracted image $S_2(i, j)$ is extremely small (the portion which slightly exists around the floc microorganisms c and the filamentous microorganisms f in FIG. 27(a)), so that two intensity peaks having substantially the same number of pixels appear. The high intensity side corresponds to the background adjacent to the microorganisms while the low intensity side corresponds to the microorganisms. Reference numeral 709 represents binarizing means which binarizes the partial extracted image $S_2(i, j)$ in accordance with the following equation (11):

$$G_3(i, j) = 0 \text{ when } G_2(i, j) > SH_3$$
$$G_3(i, j) = 1 \text{ when } G_2(i, j) \leq SH_3 \tag{11}$$

This threshold value $SH_3$ is determined by the peak value obtained by the histogram processing means 708, and the concept is the same as the method described with reference to FIG. 6.

In the binarized image $G_3(i, j)$ obtained in this manner the background near the microorganisms disappears and the clear floc microorganisms c and filamentous microorganisms f are contained in the image, as shown in FIG. 21(b). This image is stored in the memory 610.

The method of calculating the density of the filamentous microorganisms f on the basis of the image information $G_3(i, j)$ stored in the memory 610 is the same as those of the foregoing embodiments.

In accordance with this embodiment, the density is measured and calculated on the basis of the image which is processed in such a fashion that the filamentous microorganisms become clearer. Accordingly, measurement can be made more accurately.

Although we have herein shown and described several forms of apparatus embodying our invention, it is understood that various changes and modifications may be made therein within the scope of the appended claims without departing from the spirit and scope of our invention.

What is claimed is:

1. An apparatus for measuring the concentration of filamentous microorganisms in a mixture containing microorganisms, comprising:

image pickup means for magnifying an image of the mixture in a limited area in the form of a gray image and for converting the gray image into an analog luminance signal respresentative of intensity of illumination for every pixel in the gray image;

analog to digital converter means for converting the analog luminance signal into a digital signal; and processing and calculating means including an image processing unit, an image memory unit and an arithmetic unit, which are cooperatively coupled with each other for binarizing said digital signal in accordance with a predetermined intensity threshold to obtain data of a binarized image, in which pixels of a first intensity indicative of images of microorganisms within the binarized image have binary codes different from those pixels of a second intensity indicative of a background image within the binarized image; for storing the data of the binarized image in the image memory unit; for thinning the images of the microorganisms on the basis of the stored data of the binarized image until the thickness of the images of the filamentous microorganisms correspond to one pixel; for counting a number of pixels of images other than the background pixels in the binarized image which has been subject to at least the thinning process; and for calculating the concentration of the filamentous microorganisms based on said counted number of pixels and the volume of the mixture within the limited area.

2. An apparatus for measuring the concentration of filamentous microorganisms in a mixture containing the microorganisms according to claim 1, wherein said image pickup means is an underwater image pickup means to be dipped in said mixed solution and includes a sample chamber for receiving said mixed solution, and means for periodically supplying air from outside into said sample chamber to replace said mixed solution in said sample chamber.

3. An apparatus for measuring the concentration of filamentous microorganisms in a mixture containing the microorganisms according to claim 1, wherein said processing and calculating means counts said number of pixels based on the alignment direction(s) of adjacent pixels.

4. An apparatus for measuring the concentration of filamentous microorganisms in a mixture containing the microorganisms according to claim 1, wherein said processing and calculating means compares said binarized image subjected to the thinning processing in said image memory unit with the binarized image immediately preceding the thinning processing and terminates the thinning processing when there is no difference between said binarized images.

5. An apparatus for measuring the concentration filamentous microorganisms in a mixture containing the microorganisms in according to claim 1, wherein said processing and calculating means further comprises contraction processing means for cutting off one pixel from the entire periphery of the microorganism images contained in said binarized image subjected to the thinning processing, expansion processing means for adding one pixel to the entire periphery of the microorganism images contained in the binarized image subjected to the contraction processing, and mask processing means for determining the difference between said binarized image subjected to the thinning processing and said binarized image subjected to the contraction and expansion processings such that the number of pixels is counted from said difference.

6. An apparatus for measuring the concentration filamentous microorganisms in a mixture containing the microorganisms in according to claim 1, which further comprises cutting means for cutting off one predetermined pixel in said binarized image subjected to the thinning processing, and at least one pixel existing in a predetermined pattern adjacent to said one predetermined pixel.

7. An apparatus for measuring the concentration of filamentous microorganisms in a mixture containing the microorganisms according to claim 1, said processing and calculating means further comprising means for subtracting the gray image of information of the background image along, which is imaged under the state where no mixed solution exists, from the gray image information containing the microorganisms prior to binarizing said signal.

8. An apparatus for measuring the concentration of filamentous microorganisms in a mixture containing the microorganisms according to claim 1, further comprising means for enhancing the signal on the basis of the gray image information containing the microorganisms prior to binarizing said signal.

9. An apparatus for measuring the concentration of filamentous microorganisms in a mixture contianing microorganisms, comprising:

image pickup means for magnifying an image of the mixture in a limited area in the form of a gray image and for converting the gray image into an analog luminance signal respresentative of intensity of illumination for every pixel in the gray image;

analog to digital converter means for converting the analog luminance signal into a digital signal;

binarizing means for binarizing said digital signal in accordance with a predetermined intensity threshold so as to obtain data of a binarized image in which pixels of a first intensity indicative of images of the microorganisms within the binarized image have binary codes different from those pixels of a second intensity indicative of a background image within the binarized image;

image memory unit means for storing the data of the binarized image;

thinning means for thinning the images of the microorganisms on the basis of the stored data of the binarized image until the thickness of the images of the filamentous microorganisms corresponds to one pixel;

counting means for counting a number of pixels of images other than the background pixels in a binarized image which has been subject to at least the thinning process; and calculating means for calculating the concentration of the filamentous microorganisms based on said number of pixels and the volume of the mixture within the limited area.

10. An apparatus according to claim 9, wherein said image pickup means comprises an underwater image pickup means to be dipped in said mixed solution and includes a sample chamber for receiving said mixed solution and means for periodically supplying air from outside into said sample chamber to replace said mixed solution in said sample chamber.

11. An apparatus according to claim 9, wherein said counting means counts said number of pixels based on the alignment direction of adjacent pixels.

12. An apparatus according to claim 9, said thinning means further including comparison means for comparing said binarized image subjected to said thinning process with said binarized image which has not been subjected to said thinning process and for terminating the thinning process when there is no difference between said binarized images.

13. An apparatus according to claim 9, further comprising contraction processing means for cutting off one pixel from the entire periphery of the microorganism images contained in said binarized image subjected to the thinning process, expansion processing means for adding one pixel to the entire periphery of the microorganism images contained in the binarized image subjected to the contraction process, and mask processing means for determining the difference between the binarized image subjected to the thinning process and the binarized image subjected to the contraction and expansion processes, wherein the number of pixels is counted from the difference between these binarized images.

14. An apparatus according to claim 9, further comprising noise eliminating means for cutting off one predetermined pixel in said binarized image subjected to the thinning process and at least one pixel existing in a predetermined pattern adjacent to said one predetermined pixel.

15. An apparatus according to claim 9, wherein said binarizing means includes compensating means for subtracting a gray image of the background image alone, which is imaged under the condition where no mixed solution exists, from the gray image information containing the microorganisms prior to binarizing said signal.

16. An apparatus according to claim 9, wherein said binarizing means further comprises means for enhancing the microorganism image on the basis of the gray image information containing the microorganisms prior to binarizing said signal.

* * * * *